United States Patent
Rossi et al.

(10) Patent No.: US 6,627,777 B2
(45) Date of Patent: Sep. 30, 2003

(54) CATALYSTS FOR HYDRODECHLORINATION OF CARBON TETRACHLORIDE TO CHLOROFORM

(75) Inventors: Michele Rossi, Borromeo (IT); Carlo Rubini, Della Battaglia (IT); Antonio Pasquale, Novara (IT); Luigi Cavalli, Novaria (IT)

(73) Assignee: Sud Chemie MT S.R.L., Milan (IT)

( * ) Notice: Subject to any disclaimer, the term of this patent is extended or adjusted under 35 U.S.C. 154(b) by 0 days.

(21) Appl. No.: 09/973,391

(22) Filed: Oct. 9, 2001

(65) Prior Publication Data

US 2002/0077514 A1 Jun. 20, 2002

(30) Foreign Application Priority Data

Oct. 31, 2000  (IT) ..................................... MI2000A2361

(51) Int. Cl.[7] .......................... C07C 17/23; C07C 19/04; B01J 23/40; B01J 23/42; B01J 23/58
(52) U.S. Cl. ....................... 570/181; 570/260; 570/261; 502/327; 502/328; 502/330; 502/331; 502/332; 502/334; 502/339; 502/355; 502/415; 502/439
(58) Field of Search ................................. 502/334, 327, 502/328, 330, 331, 332, 339, 355, 415, 439; 570/181, 260, 261

(56) References Cited

U.S. PATENT DOCUMENTS

| | | | | |
|---|---|---|---|---|
| 3,894,963 A | * | 7/1975 | Gerdes et al. | 252/464 |
| 3,926,850 A | * | 12/1975 | Kostka | 252/455 R |
| 3,931,050 A | * | 1/1976 | Asano et al. | 252/462 |
| 3,992,331 A | | 11/1976 | Petrow | |
| 4,041,087 A | * | 8/1977 | Vannice | 260/652 R |
| 4,082,699 A | * | 4/1978 | Petrow et al. | 252/472 |
| RE29,771 E | * | 9/1978 | Cull et al. | 252/455 R |
| 4,111,848 A | * | 9/1978 | Torii et al. | 252/466 PT |
| 4,132,673 A | * | 1/1979 | Yamaguchi | 252/466 PT |
| 4,171,288 A | * | 10/1979 | Keith et al. | 252/462 |
| 4,264,475 A | * | 4/1981 | Schoennagel | 252/441 |
| 4,301,308 A | * | 11/1981 | Canavesi et al. | 568/804 |
| 4,323,542 A | * | 4/1982 | Joy, III | 423/213.5 |
| 4,451,580 A | * | 5/1984 | Butler et al. | 502/335 |
| 4,572,904 A | * | 2/1986 | Onal | 502/333 |
| 4,713,363 A | * | 12/1987 | Hucul | 502/262 |
| 4,952,543 A | * | 8/1990 | Huang et al. | 502/35 |
| 5,081,092 A | * | 1/1992 | Chattha et al. | 502/159 |
| 5,146,013 A | | 9/1992 | Dogimont et al. | |
| 5,176,897 A | * | 1/1993 | Lester | 423/659 |
| 5,192,733 A | * | 3/1993 | Mainz et al. | 502/225 |
| 5,474,965 A | * | 12/1995 | Nakatsuji et al. | 502/330 |
| 5,565,399 A | * | 10/1996 | Fraenkel et al. | 502/304 |
| 5,849,661 A | * | 12/1998 | Yamashita et al. | 502/328 |
| 5,851,948 A | * | 12/1998 | Chuang et al. | 502/314 |
| 5,880,057 A | * | 3/1999 | Hatano | 502/202 |
| 5,914,432 A | * | 6/1999 | Lume-Pereira | 570/262 |
| 6,025,297 A | * | 2/2000 | Ogura et al. | 502/300 |
| 6,083,467 A | * | 7/2000 | Takeshima et al. | 423/335 |
| 6,121,186 A | * | 9/2000 | Cauffriez et al. | 502/230 |
| 6,147,027 A | * | 11/2000 | Miyake et al. | 502/325 |
| 6,150,296 A | * | 11/2000 | Heinnerman et al. | 502/152 |
| 6,172,000 B1 | * | 1/2001 | Chattha et al. | 502/324 |
| 6,221,804 B1 | * | 4/2001 | Yamada et al. | 502/326 |
| 6,514,905 B1 | * | 2/2003 | Hanaki et al. | 502/328 |

FOREIGN PATENT DOCUMENTS

| | | |
|---|---|---|
| EP | 0 479 116 | 4/1992 |
| EP | 0 536 420 | 4/1993 |
| WO | 91 17825 | 11/1991 |

* cited by examiner

Primary Examiner—Cam N. Nguyen
(74) Attorney, Agent, or Firm—Welsh & Katz, Ltd.

(57) ABSTRACT

Catalysts for the fluid-bed hydrodechlorination of carbon tetrachloride to chloroform having high catalytic stability and comprising platinum supported on microspheroidal gamma alumina, characterized in that the platinum is in the form of particles dispersed throughout the mass of the support.

9 Claims, No Drawings

CATALYSTS FOR HYDRODECHLORINATION OF CARBON TETRACHLORIDE TO CHLOROFORM

FIELD OF THE INVENTION

The present invention relates to catalysts endowed with high catalytic stability for the production of chloroform ($CHCl_3$) starting from carbon tetrachloride ($CCl_4$) by catalytic hydrodechlorination (HDC), to the method for producing the catalysts, and to the process in which the catalysts are used.

BACKGROUND OF THE INVENTION $CCl_4$, together with chlorofluorohydrocarbons, has recently been banned (production and use) due to the intense depletion of the stratospheric layer of ozone due to this compound.

However, $CCl_4$ is formed as a main by product in the reaction for the synthesis of chloromethanes from methane and chlorine.

The disposal of $CCL_4$, typically performed by incineration, in addition to being onerous, is a considerable environmental problem.

An advantageous alternative to disposal by pyrolysis is catalytic hydrodechlorination to chloroform.

$CHCl_3$ is a useful product which does not have the environmental problems of $CCl_4$ and is therefore not subject to production and/or utilization constraints: it is in fact used in the production of the new fluorohydrocarbons, which do not interfere with the stratospheric ozone layer.

It is difficult to realize an industrial process which allows to limit the generation of unwanted chlorinated byproducts produced by the variety of reactions involved in the HDC process and to work with catalysts which maintain their activity substantially unchanged for a sufficiently long time, due to the fact that the above cited reactions are highly exothermic and because of the ease with which the catalyst can be poisoned by the hydrogen chloride generated during the reactions and/or by contamination by carbon-containing byproducts.

A sufficiently high selectivity can be achieved by working with low conversions and high hydrogen/$CCl_4$ ratios; however, these conditions are of no practical interest.

Patent literature reports various methods for maintaining a high stability of the catalyst and reducing the generation of byproducts.

U.S. Pat. No. 5,105,032 describes catalysts based on Pt supported on oxides having a large surface area, in which the catalysts are pretreated at the temperature of 200° C. or higher with hydrogen chloride (before or during reduction with hydrogen) in order to give the catalyst high resistance to deactivation.

The hydrodechlorination reaction is preferably performed in the presence of HCl, using $CCl_4$:HCl ratios between 1:1 and 1:2.

An excess of HCl has the effect of lowering conversion but increases selectivity. Platinum is preferably used in a mixture with promoters such as Sn, Sb, Bi, Ti, Pb and mixtures thereof.

The above cited patent describes that a commercial catalyst containing Pt supported on gamma alumina and not previously treated with HCl loses its activity already after a few hours of reaction.

Because of pretreatment with HCl at high temperatures and of the need to proceed by reaction in the presence of significant concentrations of HCl, the above cited process is of limited practical interest.

EP-A-570020 describes a catalyst for HDC which comprises Pt supported on alumina having a surface area of less than 100 $m^2$/g, mainly constituted by alpha, theta or delta alumina or mixtures thereof according to the calcination temperature.

Applied Catalysis A. General 174 (1998) 33–39 describes a catalyst containing Pt supported on gamma alumina which has high resistance to aging and is obtained by treating with an aqueous solution of $NH_4Cl$ at ambient temperature a commercial catalyst based on Pt supported on gamma alumina.

Treatment with $NH_4Cl$ has the effect of increasing the size of the Pt particles, which are mostly smaller than 0.5 nm and are arranged in an egg-shell configuration on the supporting particle.

In the treated catalyst, the particles have a size of 5 to 8 nm.

The high reactivity with HCl and CCl of the crown of relatively small particles of Pt, which are also in a state of considerable electron deficit, is thought to be responsible for the poisoning of the catalyst on the part of HCl.

In the untreated and deactivated catalyst, most of the Pt is in the form of chloride, $Pt_n Cl_x$.

The treated catalyst maintains a substantially constant conversion and selectivity (between 70 and 80%) for over 2000 hours.

The aim of the present invention is to provide a catalyst for hydrodechlorination of $CCl_4$ to $CHCl_3$ containing Pt supported on gamma alumina which maintains its high activity and selectivity for $CHCl_3$ substantially unchanged for sufficiently long periods without having to subject the catalyst to activation pretreatments.

This aim and other objects are achieved with the catalyst according to the invention.

BRIEF DESCRIPTION OF THE INVENTION

It has been found unexpectedly that it is possible to obtain catalysts based on Pt supported on gamma alumina which have high activity and selectivity in the reaction for hydrodechlorination of $CCl_4$ to $CHCl_3$ and are able to maintain their catalytic performance practically unchanged for very long periods (2000 hours and more) if the catalyst is prepared in conditions which allow the platinum to be dispersed throughout the mass of the supporting particle instead of only on the surface layer, as occurs in conventional catalysts containing platinum supported on gamma alumina.

DETAILED DESCRIPTION OF THE INVENTION

In the catalysts according to the invention, more than 50% of the Pt particles have dimensions between 2 and 10 nm (Transmission Electron Microscopy (TEM) measurements with 0.21 nm resolution). SEM (Scanning Electron Microscopy) measurements have demonstrated that platinum is distributed throughout the entire particle of the support.

The distribution of the platinum within the alumina particle is deduced from the value of the Al/Pt ratio along a diameter of the cross-section of the particle of catalyst, comparing this ratio with the value of the theoretical Al/Pt ratio determined by chemical analysis.

The position of the measured value is expressed as a percentage of the length of the diameter. The values found in particles of different samples of catalyst approximate the theoretical or nominal ratio.

In some particles, the ratio is lower or higher than the theoretical ratio; in others, the values are more uniform and closer to the theoretical value. In any case, however, the platinum is diffused throughout the entire mass of the particle of the support.

Preferably the support is constituted by microspheroidal alumina with an average particle diameter between 30 and 70 microns, in which there are no particles with diameters exceeding 120–130 microns and less than 5% of the particles have a diameter of less than 20 microns.

The surface area is 110–220 $m^2/g$; pore volume is 0.3–0.6 $cm^3/g$; the average radius of the pores is 4–8 nm.

The catalyst is prepared by impregnating the alumina particles with a solution of a water-soluble compound of Pt, preferably hexachloroplatinic acid or $PtCl_2$, using an amount of solution lower than the total volume of the pores, preferably 0.7–0.9 times the volume of the pores.

Impregnation is performed by adding, drop by drop, the solution of the Pt compound to the fluidized alumina or by spraying the solution on the alumina particles in a rotating vessel.

The impregnated alumina is dried (for example at 140–160° C. for 16 hours) and then treated with an aqueous solution of formic acid or of an alkali formate in order to reduce the platinum compound to platinum metal.

This is done, for example, at 70 to 110° C. in a stream of nitrogen which dilutes the released hydrogen (during the initial step, the temperature is kept at 70–75° C. for 2–3 hours and is then raised and kept at 100° C. for 2–3 hours).

This is followed by the final step for drying at 140–150° C. for 12–16 hours.

The reduction of platinum with hydrogen according to conventional methods (at 200° C. or at higher temperatures) does not allow to obtain catalysts having the intended characteristics.

Platinum is present in the catalysts in amounts between 0.05 and 3% by weight with respect to the support, preferably 0.1 to 1% by weight.

Promoters such as Sn, Ti, Ge, Rh, Si, Pb, P, As, Sb, Bi, Cu, Ag, Co, W and mixtures thereof can be present in an atomic ratio of less than 1 with respect to Pt. Oxides of Be, Mg, Ca and/or Ba can be present in an atomic ratio with Pt of 0.1 to 50 or more. The oxides have a favorable effect on the catalyst selectivity. MgO is preferred.

The hydrodechlorination reaction is preferably carried out in a fluid bed, in which the hydrogen is used as fluidizing gas fed in equicurrent with $CCl_4$ and with recycled $CH_4$ and/or with an inert gas.

The $H_2/CCl_4$ molar ratio is from 3 to 20. When the ratio is lower than 3, a significant amount of $C_2Cl_4$ is generated and the catalytic activity rapidly decreases.

The reaction temperature is from 90° to 170° C.: if the temperature is increased, conversion increases significantly, while selectivity decreases moderately.

The hourly space velocity (WHSV) is 0.5–3 kg $CCl_4$/kg.hr of catalyst.

If the $CCl_4$ load is increased, the productivity of the system increases at the expense of a small sacrifice in conversion.

The methane formed as byproduct (substantially the only hydrocarbon byproduct, since chlorinated hydrocarbons are substantially absent) is advantageously recycled together with the excess hydrogen.

This allows to avoid methane/hydrogen separation.

The hydrogen chloride produced during the reaction can also be recycled up to reach a percent of 60% by volume at the entrance of the reactor without negative effects on the performance of the catalyst.

The following examples are given to illustrate but not to limit the scope of the invention.

EXAMPLE 1

1) Preparation of the Platinum-Containing Catalyst Supported on Microspheroidal Alumina 1400 g of 30/180 Condea gamma alumina, 180 $m^2/g$ B.E.T., pore volume 0.5 $cm^3/g$, particle size listed in Table 1;

27.51 g of hexachloroplatinic acid ($H_2PtCl_6$) with 40.21% Pt (Johnson Matthey);

500 ml of demineralized water.

The gamma alumina is placed in a 4-liter polyethylene jar and is turned clockwise in a trundler.

The solution of hexachloroplatinic acid is transferred into a glass sprayer provided with a nozzle and is transferred, by means of a slight pressure of nitrogen, in approximately 2 hours, onto the alumina.

The system is left to rotate for 1 hour in order to ensure complete homogenization.

The product is dried at 145° C. for one night.

The result is 1440 g of unreduced catalyst.

2) Activation of the Catalyst By Reduction of Platinum with Formic Acid

The following are used 900 g of alumina impregnated as described above;

880 ml of demineralized water;

118 ml of 99% formic acid (HCOOH) (C. Erba).

Reduction is performed in a Rotavapor with a 3-liter flask provided with 4 flow breakers.

900 g of alumina impregnated with the platinum compound are added to 50 ml of formic acid in 880 ml of $H_2O$ (5.4% solution of formic acid).

After 2 hours of mixing, the disperse system is uniform and has a whitish color.

Using an oil bath, the mass is heated to 75° C., keeping the reagents at this temperature for 2 hours.

The temperature is raised to 100° C. in three hours; during this period, and after every hour, 25 ml, 25 ml, and 18 ml of 99% HCOOH are added sequentially. The temperature of the bath is raised to 110° C. and the reduction step is completed in approximately one hour.

Nitrogen is injected onto the surface of the rotating mass and most of the dispersed water is stripped by means of a slight vacuum produced by a mechanical pump. The resulting mass, which has a deep brown color, is dried at 160° C. for one night.

900 g of reduced catalyst (Catalyst A) are obtained.

The catalyst was used in tests for $CCl_4$ hydrodechlorination (tests 1.1–1.6); the conditions and results are listed in Table 2.

COMPARISON EXAMPLE 1

Preparation of Platinum-Containing Catalyst Supported on Microspheroidal Alumina, Reduced with Hydrogen 100 g of 30/180 Condea gamma alumina;

2.45 g of hexachloroplatinic acid with 40.91% Pt, corresponding to 1 g of platinum;

50 ml of demineralized water.

The alumina to be impregnated is placed in a 250-ml beaker, the hexachloroplatinic acid is dissolved in water in another 100-ml beaker and is poured rapidly over the solid.

Using a glass rod, rapid mixing is performed until the disperse system assumes a straw yellow color and is entirely uniform.

The impregnated alumina is dried in a stove for one night at 145° C., obtaining 103 g of product.

100 g of alumina as specified above are placed in a large 300-ml test tube and degassed of air by means of a gaseous flow of nitrogen. Heating is performed by means of a jacket which allows to reach high temperatures.

Heating to 370° C. is performed by means of an electric jacket, sending into the container a mixture of nitrogen (1.5 l/h) and hydrogen (1.5 l/h).

The flow of nitrogen is interrupted while the flow of hydrogen is increased to 3 l/h.

The temperature and the flow are maintained as above for 5 hours.

The flow of hydrogen (3 l/h) and nitrogen (3 l/h) is cooled, then only nitrogen is fed.

100 g of reduced catalyst (Catalyst B) are obtained.

The catalyst was used in $CCl_4$ hydrodechlorination tests (tests 1–6); the conditions and results are listed in Table 2.

EXAMPLE 2

1) Preparation of Platinum- and Magnesium-Containing Catalyst Supported on Microspheroidal Alumina 220 g of 30/180 Condea gamma alumina, 180 $m^2$/g B.E.T., pore volume 0.5 ml/g, particle size listed in Table 1;

29.6 g of magnesium acetate * 4 $H_2O$ (Carlo Erba), equivalent to 3.35 g Mg;

260 ml of demineralized water.

Impregnation is performed in a Rotavapor with a 1-l flask provided with flow breakers.

The alumina is placed in the flask with 200 ml of demineralized water and rotated for 1 h so as to obtain a uniform powder. A solution, prepared in a 100-ml beaker, of magnesium acetate dissolved in 60 ml of demineralized water is then poured into the flask.

The flask is rotated again for 30 minutes at ambient temperature, then the bath of the Rotavapor is heated to 100° C. for 30 minutes. Under a slight vacuum generated by a mechanical pump, 120 ml of water are distilled in 1.5 h. The moist solid is transferred into a capsule and dried at 110° C. for 12 h in a muffle. The temperature is then raised to 400° C. in 4 hours and maintained for 12 hours, introducing a stream of air into the muffle. In this manner, the magnesium acetate is decomposed, forming magnesium oxide.

230.5 g of alumina containing magnesium oxide are obtained.

210 g of alumina with magnesium oxide 4.1 g of hexachloroplatinic acid with 41.29% Pt (corresponding to 1.69 g of platinum)

82 ml of demineralized water are used to prepare the catalyst according to Example 1. After spraying, the product is dried in a stove at 150° C. for 16 hours.

202 g of unreduced catalyst are obtained and are subjected to reduction with formic acid.
The following are used 192 g of alumina with 0.8% Pt, 1.52% Mg;

26 ml of 99% formic acid (C. Erba)

180 ml of demineralized water

Reduction is performed in a Rotavapor with a 1-l flask provided with 4 flow breakers.

A solution of 180 ml of demineralized water containing 14 ml of formic acid is poured onto the alumina. The flask is rotated at ambient temperature for 1 h, then 5 ml of formic acid are added. The temperature is raised to 65° C., keeping it constant for 1.5 hours, and then to 90° C. for 4 hours. The remaining formic acid is added during this period.

Under a slight vacuum in a nitrogen atmosphere, 70 ml of water are eliminated.

The flask is placed in a stove at 90° C. for 63 h and at 150° C. for 15 h.

190 g of reduced catalyst (Catalyst D) are obtained.

Tests 7 and 8 (Table 2) were performed with this catalyst. The chemical and physical properties of Catalyst D are listed in Table 1.

COMPARISON EXAMPLE 2

50 g of pelletized alumina in cylinders of the TH type, calcined at 550° (three-lobed cylinders with through holes at the lobes, with an axis which is equidistant and parallel to the axis of the cylinder, a height of 5 mm, a diameter of the circumscribed circumference equal to 3.3 mm, and a hole diameter of 1.7 mm)

1.23 g of 40.91% hexachloroplatinic acid, corresponding to 0.5 g of platinum;

20 ml of demineralized water.

The TH alumina particles are placed in a 100-ml beaker and the aqueous solution of hexachloroplatinic acid is poured rapidly onto them, mixing with a glass rod. After a few minutes, the support is found to have absorbed the entire solution.

The alumina is placed to dry in a stove at 145° C.

50 g of unreduced catalyst are obtained after cooling.

50 g of TH alumina impregnated with the above described methods are treated with hydrogen, using the same apparatus for feeding nitrogen and hydrogen and the same heating apparatus used in the case of comparison example 1.

The mixture of 3 l/h of hydrogen and nitrogen (1:1 vol.) is fluxed until the temperature is reached, keeping the temperature and the flow constant for two hours. Cooling in a stream of nitrogen and hydrogen and then only constant nitrogen.

50 g of product (Catalyst C) are obtained.

The catalyst was used in a hydrodechlorination test in a fixed bed operating at atmospheric pressure; the conditions and results are listed in Table 2.

The hydrodechlorination tests were conducted in fluid-bed and fixed-bed reactors. The fluid-bed reactor is preferred because it allows better removal of heat and an isothermic thermal profile.

Two fluid-bed reactors were used: a laboratory reactor, made of glass, and an industrial reactor, made of steel.

The first reactor is of the tubular type, provided at its base with a G3 porous partition for homogenizing the reacting gases and with an outer jacket for removing the heat of the reaction. Length is 300 mm, inside diameter is 45 mm, and jacket inside diameter is 75 mm. A glass coil in the jacket preheats the gases before entering the reactor.

The second reactor is similar to the first one, but its length is 2000 mm and its inside diameter is 100 mm.

Both reactors were used for the fluid-bed process, while the glass reactor was also used for the fixed-bed process.

Temperature control of the reactor is performed by means of a thermostatic bath; silicone oil is used as fluid.

The carbon tetrachloride is dosed by means of a membrane pump, evaporated at low temperature and mixed with hydrogen, nitrogen or methane, dosed by mass-flow flow-rate detectors.

In tests 6, 7 and 8, the carbon tetrachloride was dosed by saturation of a stream of nitrogen at controlled temperature;

the flow-rate of the nitrogen was controlled by mass-flow. The amount of $CCl_4$ sent to the reaction is conditioned by the temperature of the saturation column, which is kept constant with a thermostatic bath, and is placed over a flask which contains the boiling $CCl_4$.

In the case of the fluid-bed experiments (1–8 in Table 1), the reaction mixture is stabilized at the chosen temperature and fed to the reactor through the porous partition; the temperature of the reactor is controlled by the silicone oil. An isothermic profile was obtained in all the tests.

The reaction temperature is measured by a thermocouple which is located in a sheath inside the catalytic bed and can be moved easily along the bed.

The movement of the gas is upward from below.

The off-gases are cooled in a first trap placed in a Dewar vessel and cooled to −65° C. in order to condense the chlororganics, and are then sent to a second trap which contains a 5% aqueous solution of NaOH, where the hydrogen chloride is absorbed. The chlororganics are analyzed by means of a Carlo Erba HRGC chromatograph and a CP-SIL 5 B NO 7770 separation column.

The chloride anion is determined argentometrically.

In the case of the CPR1 and CPR2 tests, the steel and glass reactors respectively, loaded with palletized catalyst, were used.

The reaction conditions and the operating conditions are listed in Table 2.

The disclosures in Italian Patent Application No. MI2000A002361 from which this application claims priority are incorporated herein by reference.

TABLE 1

|  |  | Alumina powder | | | | Alumina granules | |
|  |  | | Catalyst | | | | Catalyst |
| FORM | | Support | A | B | D | Support | C |
| Chemical properties | | | | | | | |
| Pt | % w | — | 0.80 | 1.00 | 0.80 | — | 1.0 |
| Mg | % w | — | — | — | 1.52 | | |
| SIO2 | % w | 0.015 | 0.015 | 0.015 | 0.015 | 0.1 | 0.1 |
| Fe2O3 | % w | 0.01 | 0.015 | 0.015 | 0.015 | 0.04 | 0.04 |
| Na2O | % w | 0.005 | 0.005 | 0.005 | 0.005 | 0.03 | 0.03 |
| SURFACE PROPERTIES(*) | | | | | | | |
| Al | Atom % | — | 40.1 | — | — | — | — |
| O | Atom % | — | 53.4 | — | — | — | — |
| Pt | Atom % | — | 0.16 | — | — | — | — |
| Cl | Atom % | — | 1.5 | — | — | — | — |
| PHYSICAL PROPERTIES | | | | | | | |
| Surface area (BET) | m2/g | 180 | 190 | 180 | 178 | 225 | 220 |
| True density | g/ml | | 3.29 | | 3.27 | 3.2 | 3.2 |
| Particle density | g/ml | | 1.3 | | 1.39 | 1.1 | 1.1 |
| Pore volume | ml/g | 0.45 | 0.46 | 0.41 | 0.41 | 0.55 | 0.55 |
| Bulk density | g/ml | 0.75 | 0.75 | 0.75 | 0.76 | — | — |
| PARTICLE SIZE DISTRIBUTION | | | | | | | |
| >125 | Microns | 0.1 | 0.3 | 0.3 | 0.3 | — | — |
| 125–90 | Microns | 5.5 | 5.0 | 5.2 | 5.1 | — | — |
| 90–63 | Microns | 22.3 | 19.4 | 21.0 | 22.4 | — | — |
| 63–40 | Microns | 40.3 | 48.8 | 45.0 | 44.5 | — | — |
| <40 | Microns | 31.8 | 26.3 | 28.0 | 27.5 | — | — |
| <20 | Microns | <2 | 0.2 | 0.2 | 0.2 | — | — |

(*) Surface analysis determined by XPS

TABLE 2

| Reactor | Unit of measure | Tests | | | | | | | | CPR 1 | CPR 2 |
|  |  | 1 | 2 | 3 | 4 | 5 | 6 | 7 | 8 | | |
| Type | | | | | | | | | | | |
| a = fluid | | a | a | a | a | a | a | a | a | a | |
| b = fixed | | | | | | | | | | | b |
| MATERIAL | | | | | | | | | | | |
| c = glass | | c | c | c | c | d | c | c | c | | |
| d = stainless steel | | | | | | | | | | d | d |
| Fed $CCl_4$ | Mol/h | 0.55 | 0.676 | 0.717 | 0.674 | 16.58 | 0.474 | 0.616 | 0.787 | 0.456 | 0.102 |
| Space velocity | $CCl_4$ milli M/g cat $h^{-1}$ | 11 | 13.5 | 14.3 | 13.5 | 12.8 | 9.48 | 12.3 | 15.7 | 7.4 | 8.3 |

TABLE 2-continued

| Reactor | Unit of measure | Tests | | | | | | | | | |
|---|---|---|---|---|---|---|---|---|---|---|---|
| | | 1 | 2 | 3 | 4 | 5 | 6 | 7 | 8 | CPR 1 | CPR 2 |
| Temperature | | | | | | | | | | | |
| Oil bath | °C. | 102 | 97 | 90 | 85 | 100 | 116 | 115 | 115 | 102 | 102 |
| Reactor | °C. | 117 | 110 | 105 | 99 | 108 | 133 | 133 | 134 | 111 | 124 |
| $H_2/CCl_4$ ratio | Molar | 10.2 | 8.15 | 7.6 | 8.15 | 16 | 7.63 | 6.07 | 4.11 | 18.6 | 13.4 |
| Diluents | | | | | | | | | | | |
| $N_2$ | % vol. | — | — | — | — | 50 | 50 | 50 | 48 | — | — |
| $CH_4$ | % vol. | — | 50 | 50 | 50 | — | — | — | — | — | — |
| Duration | h | 2 | 5 | 7 | 6.5 | 323 | 20 | 20 | 50 | 3 | 9 |
| Conversion | % | 97.5 | 92.6 | 92.0 | 88.0 | 92.6 | 91.5 | 92.0 | 80.3 | 92.0 | 83.7 |
| Selectivity | % Molar | | | | | | | | | | |
| $CHCl_3$ | " | 74.9 | 81.7 | 81.0 | 83.0 | 84.4 | 71.6 | 81.4 | 85.0 | 69.4 | 67.0 |
| $CH_2Cl_2$ | " | 1 | — | — | — | — | 2.8 | 1.0 | — | 0.7 | 2 |
| $CH_4$ | " | 24 | 17.8 | 18.9 | 17 | 14.8 | 25.7 | 17.5 | 15 | 29 | 30 |

What is claimed is:

1. A catalyst for hydrodechlorination of carbon tetrachloride to chloroform, comprising platinum supported on gamma alumina, particles, wherein the platinum is distributed throughout the entire mass of the alumina particles.

2. The catalyst according to claim 1, wherein the platinum is present in an amount from 0.05 to 3% by weight on the support.

3. The catalyst according to claim 1, wherein the platinum is in form of particles having a size of 1 to 12 nm.

4. The catalyst according to claim 1, wherein the gamma alumina is in form of microspheroidal particles having an average diameter of 30 to 70 microns.

5. The catalyst according to claim 1, wherein the gamma alumina has a surface area of 110 to 240 $m^2/g$.

6. The catalyst according to claim 1 further comprising, metals selected from the group consisting of Sn, Ti, Ge, Si, Pb, P, As, Sb, Bi, Cu, Ag, Co, W, and mixtures thereof.

7. The catalyst according to claim 1, further comprising an oxide selected from the group consisting of Be, Mg, Ca, Ba, and mixtures thereof.

8. A process for hydrodechlorination of carbon tetrachioride with hydrogen to chloroform, using the catalyst according to claim 1 wherein the hydrodechlorination is conducted in a fluidized bed at a temperature of from 90 to 170° C. and with $H_2/CCl_4$ ratios of 3 to 20.

9. The process according to claim 8, wherein methane is formed as a byproduct, and excess hydrogen and hydrogen chloride generated during the process are recycled to a hydrodechlorination reactor.

* * * * *

UNITED STATES PATENT AND TRADEMARK OFFICE
CERTIFICATE OF CORRECTION

PATENT NO. : 6,627,777 B2
DATED : September 30, 2003
INVENTOR(S) : Michele Rossi et al.

It is certified that error appears in the above-identified patent and that said Letters Patent is hereby corrected as shown below:

<u>Title page,</u>
Item [75], Inventors, delete "Luigi Cavalli, Novaria (IT)" and replace with -- Luigi Cavalli, Novara (IT) --

Signed and Sealed this

Fifteenth Day of February, 2005

JON W. DUDAS
*Director of the United States Patent and Trademark Office*